(12) United States Patent
Pitochelli et al.

(10) Patent No.: US 6,451,253 B1
(45) Date of Patent: Sep. 17, 2002

(54) HIGH CONCENTRATION CHLORINE DIOXIDE GEL COMPOSITION

(75) Inventors: Anthony R. Pitochelli, Witchita, KS (US); Jennifer R. Miller, Houston, TX (US)

(73) Assignee: Vulcan Chemical Technologies, Inc., West Sacremento, CA (US)

( * ) Notice: Subject to any disclaimer, the term of this patent is extended or adjusted under 35 U.S.C. 154(b) by 0 days.

(21) Appl. No.: 09/291,778

(22) Filed: Apr. 14, 1999

(51) Int. Cl.⁷ .................................................. A61L 9/00
(52) U.S. Cl. ........................... 422/29; 422/29; 422/37; 424/661; 424/665; 423/472; 423/477; 252/187.21
(58) Field of Search ...................... 422/29, 37; 429/661; 424/665, 472; 423/477; 252/187.21

(56) References Cited

U.S. PATENT DOCUMENTS

| 3,741,805 A | 6/1973 | Crotty et al. |
| 4,861,514 A | 8/1989 | Hutchings |
| 5,051,252 A | 9/1991 | Schultz et al. |
| 5,104,660 A | 4/1992 | Chvapil et al. |
| 5,360,574 A | 11/1994 | Iwahashi |
| 5,597,561 A | 1/1997 | Kross |
| 5,616,347 A | 4/1997 | Alliger et al. |
| 5,651,996 A | * 7/1997 | Roozdar ................. 422/29 |

* cited by examiner

Primary Examiner—Robert J. Warden, Sr.
Assistant Examiner—Imad Soubra
(74) Attorney, Agent, or Firm—Leonard Bloom; Sam Rosen

(57) ABSTRACT

High concentration chlorine dioxide gel compositions are prepared for disinfectant, deodorizing and for like uses. The preferred gel compositions are prepared from xanthan, guar or like gums.

10 Claims, No Drawings

HIGH CONCENTRATION CHLORINE DIOXIDE GEL COMPOSITION

FIELD OF THE INVENTION

Field of the Invention

The herein disclosed invention is directed to chlorine dioxide formulations to be applied as disinfectants, deodorants, topical preparations and for like uses. More specifically, the invention is involved with the preparation gels of chloride dioxide to be used as disinfectants, deodorants and the like.

BACKGROUND OF THE INVENTION

While there is much literature describing chloride dioxide gels, there is a need in the industry for gel products with controlled amounts of chlorine dioxide and which are easy to prepare. In addition to ease of preparation, there is a need for gel compositions with high concentrations of chlorine dioxide.

The gums employed as the gels or thickeners of this invention are generally supplied as powders and with the addition of water, thicken and become a gel.

The patent literature contains references to the use of gels for various applications ranging from a biocidal wound dressing, skin sterilants, veterinarian applications, treatment of skin conditions such as psoriasis, fungal infections, eczema, dandruff, acne, genital herpes lesions, and leg ulcers. Chlorine dioxide gels made in situ by mixing a chlorite containing gel with a lactic acid gel have been cited for prevention of transmission of HIV virus. Gels have also been cited as anti-inflammatory agents for reducing various tissue inflammations.

Prior Art Patents

A review of the patent literature on the topic of the preparation of chlorine dioxide containing gels, discloses prior art patents which involve the use of sodium chlorite as the precursor for chlorine dioxide preparations, along with some method of converting said chlorite to chlorine dioxide at the time of use.

The one patent which claims chlorine dioxide as an actual component in a gel is the Hutchings Patent, U.S. Pat. No. 4,861,514. Hutchings mixes chlorite and "initiator". Included among the "initiators" is hydroxalklycelluloses, alkali metal alginates, xanthan gum, cargeenen, agar and compounds containing an aldehyde substituent group. Methyl cellulose and sodium carboxymethylcellulose were found not to be initiators. The sodium chlorite disclosed in the patent is used at a concentration of 0.01 to 1% by weight, and the initiator is used at levels greater than 0.05, and preferably above 0.1%. Dyes, perfumes and reducing sugars were also included in the mix. Hutchings claims a chlorine dioxide equilibrium concentration formed within a week of 0.1 to about 10 ppm, with a preferable concentration 0.1 to 2 ppm (column 7, line 9). The patent claims disinfection at greater than 1 ppm chlorine dioxide, and cleaning and sanitizing at about 2 ppm. The chlorine dioxide achieves an equilibrium at a low concentration. With the equilibrium concentration of chlorine dioxide is from 0.1 to about 10 ppm and preferably 0.1 to 2 ppm, it can be readily discerned that the concentration of chlorine dioxide taught by Hutchings does not come close to that desired in the present invention.

U.S. Pat. No. 4,861,514 cites formation of chlorine dioxide from chlorite and xanthan gum initiator. As chlorine dioxide reacts with organics, or decomposes spontaneously, chlorite is one of the decomposition products. Formed chlorite would be encouraged to reform chlorine dioxide by reaction with the acid functionality inherent in the xanthan gum, supporting the claim of gel stability using xanthan gum. Hutchings (U.S. Pat. No. 4,861,514) actually uses this chemistry to make his chlorine dioxide in situ. This stability is in contrast to the behavior of xanthan gum in the presence of other oxidants, such as persulfates, peroxides and hypochlorites, all of which depolymerize xanthan gum. As manufactured either as a 25% aqueous solution, or an 80% solid, sodium chlorite contains alkalinity to provide chemical stability. The chlorite is inert and does not convert to chlorine dioxide in a high pH environment. Addition of acid is required to promote conversion to chlorine dioxide. If the acidity is provided by xanthan gum alone, without the addition of any other organic or inorganic acids, then the amount of chlorite which can be included in the mix is limited, since the accompanying alkalinity of the chlorite partially neutralizes the acidity of the xanthan gum, preventing conversion of chlorite to chlorine dioxide. This limits the final concentration of chlorine dioxide which can be prepared in the absence of additional added acid to less than 200 ppm. Hutchings does not state this, but he is claiming only very dilute chlorine dioxide systems, and therefore is out of the range of gel concentration possible with the herein disclosed invention.

Crotty et al in U.S. Pat. No. 3,741,805 teaches a cleaning and sanitizing composition containing xanthan gum. Chlorine compounds are mentioned, but chlorine dioxide is not mentioned.

Iwahashi in U.S. Pat. No. 5,360,574 discloses a polyethylene-imine gel system containing chlorine dioxide. The system with the gel is actually a chlorite which is stabily stored in alkali and becomes active in acid (column 1). Iwakhashi is not, in fact, pertinent for while the patent refers to "stabilized chlorine dioxide" the product of the patent is actually a solution of sodium chlorite which has an alkaline pH. This high pH is necessary in order to insure the stability of the product. In short, the Iwakhashi product is sodium chlorite and not chlorine dioxide.

In brief, the prior art processes, unlike the instant invention, do not start with chlorine dioxide per se in solution and thicken, but rather start with chlorite which when mixed with an acid-containing gel partially converts to chlorine dioxide after mixing.

Objects of the Invention

This invention has for an object the efficient preparation of chlorine dioxide gels.

Another object of this invention is the preparation of chlorine dioxide formulations in chlorine dioxide concentrations not attained by the prior art.

A significant object of this invention is to prepare a gel composition with high concentrations of chlorine dioxide.

These and other objects of the present invention will become apparent from a reading of the following specification.

BRIEF SUMMARY OF THE INVENTION

Detailed Description of the Invention

The herein disclosed invention sets forth the novel methods for preparing higher concentrations of chlorine dioxide gel compositions. Involved are two types of chlorine dioxide gels, namely, those formed directly from aqueous chlorine dioxide solutions and added thickeners; and those formed by adding a specific thickener to dilute chlorite solutions, and having the chlorine dioxide generated spontaneously on storage.

Gels of this invention are novel in that the chlorine dioxide solution is prepared before the gelling action takes place, so that the concentration of the final gel can be set to any desired level beforehand by using a chlorine dioxide solution with a concentration appropriate for the intended application. The gels may be used as is without any need for additional mixing or preparation. This method allows preparation of gels with a wide range of concentrations. The use of xanthan gum as the thickener is most preferred because this polysaccharide has acid functionality which contributes to the stability of the chlorine dioxide in the gel.

Gels using various quantities of xanthan gum thickener and aqueous chlorine dioxide were prepared. It was observed that xanthan gum appeared to improve chlorine dioxide storage stability. Systems of aqueous chlorine dioxide mixed with guar gel, xanthan gel, and a mix of guar and xanthan gel all retained high levels of chlorine dioxide in the gel, but the systems with the highest levels of xanthan gum retained more chlorine dioxide than similar concentrations of guar gel. There are three possible reasons for this:

1. The higher viscosities help retain chlorine dioxide in the gel phase by reducing diffusion and consequent volatility.
2. The acid functionality on the xanthan gum polysaccharide polymer improves chlorine dioxide stability and encourages chlorine dioxide formation from any chlorite present in the mix.
3. Or a combination of reasons 1 and 2.

Following these observations, the inventor was able to demonstrate spontaneous generation of chlorine dioxide from aqueous solutions of solid 80% sodium chlorite and xanthan gum. While U.S. Pat. No. 3,741,805 cites the use of xanthan gum as a thickener for a sanitizing liquid prepared from a chlorine generator such as chlorinated trisodium phosphate, chlorinated isocyanurates or sodium hypochlorite (chlorite is not mentioned), this system is prepared at the time of use because xanthan gum gels do not have long term stability in the presence of the hypochlorite oxidizer present in the final solution. (See Kelco Bulletin, "Xanthan Gum, Natural biogum for scientific water control, fifth edition, page 11.)

There are several U.S. and foreign patents which describe chlorine dioxide gels which are prepared by mixing two gels at the time of use; one gel containing sodium chlorite precursor, and the other an organic acid such as lactic acid. U.S. Pat. No. 4,861,514 cites the preparation of compositions containing chlorine dioxide prepared from sodium chlorite and an initiator, with xanthan gum included in the list of possible initiators. In this respect, the reaction between chlorite and xanthan gum is not novel, but is cited to illustrate the benefit derived from the acid functionality of the xanthan gum in contributing to the stability of the chlorine dioxide gels. Using xanthan gum thickener, the generation of chlorine dioxide starting with dry 80% solid sodium chlorite is concentration sensitive. Increasing the level of solid 80% chlorite tenfold does not result in increased chlorine dioxide formation. As manufactured, this chlorite contains 20% inert diluents. Two of the components of the diluent are carbonate and caustic. These components will neutralize the organic acid functionality of the xanthan molecule and raise the pH of the system to the point where all the acidity is neutralized, at which point little or no chlorine dioxide is formed. The benefit of increased chlorite levels must be balanced against the increased alkalinity which accompanies the chlorite to the point where chlorite conversion is not totally inhibited. Use of liquid chlorite solutions in place of the dry sodium chlorite will pose similar problems since as manufactured, these solutions contain caustic added to stabilize the chlorite. The consequence of this chemistry is that preparation of chlorine dioxide gels by this route is limited to the formation of dilute gels containing at most only a few hundred parts per million chlorine dioxide. Novelty of the instant invention resides in the following features:

The chlorine dioxide already exists in its use concentration at the time the thickener is added.

Any conventional generation process can be used to prepare the chlorine dioxide.

The chlorine dioxide can be prepared by the dry mix process immediately prior to gel preparation.

The dry mix can contain the gelling agent so that gelling takes place during chlorine dioxide formation.

The attractiveness of the herein disclosed invention is that stable chlorine dioxide gels can be prepared directly in a single step by adding the appropriate thickeners to chlorine dioxide solution per se or the addition of chlorine dioxide solution to the gel, or by adding water to the dry mix containing the gelling agent.

Gels up to and including 6000 ppm are possible with the novel preparation method of this invention. The gels can be used for a broad spectrum of applications, from topical application to kill bacteria, viruses and fungi, to non-personal applications to control odors or sterilize enclosed spaces. Xanthan gum gels are very pleasant to the hand and can perform the function of lubrication during application. On drying, a thin film of solid xanthan remains at the pont of application.

Gels have also been formed by vigorous blending of sodium carboxymethylcellulose into aqueous chlorine dioxide. These gels can be prepared in extremely viscous form, and appear to be very stable, suffering chlorine dioxide loss by volatility only. These gels would be very well suited to applications where slow volatilization of chlorine dioxide is desired, such as atmospheric disinfection.

Xanthan gum is the preferred thickener because its acid functionality lowers gel pH and since chlorine dioxide is stable in an acid environment. Xanthan gum contributes to the stability of the chlorine dioxide in the gel.

While as a whole the main part of this invention was carried out with xanthan gum and guar gum, other gums would be operative as understood by those skilled in the art. Sodium caryboxymethylcellulose would be an operative gel. In addition, the main criteria for operative gums is the need for the gum to be stable and compatible with chlorine dioxide. The gum should be resistant to oxidation by the chlorine dioxide, and preferably the gel formed should have a low pH.

Because the chlorine dioxide is prepared at the use concentration before gelling, the final gel can contain any desired level of chlorine dioxide by adjusting the concentration of the aqueous chlorine dioxide solution prior to the addition of the gelling agent.

Once the chlorine dioxide gel is formed of the desired concentration, other additives such as colorants and stabilizers can be added, depending on the end use (e.g. disinfectant, deodorizer, etc.) as readily understood by those skilled in the art.

In its broadest aspect, this invention envisions a method for preparing a chlorine dioxide gel comprising the steps of preparing a solution of chlorine dioxide and adding said solution of chlorine dioxide to a gum thickener to form a gel containing chlorine dioxide, or alternatively the method for preparing a chlorine dioxide gel comprising the steps of preparing a solution of chlorine dioxide and adding a gum thickener to said solution of chlorine dioxide to form a gel containing chlorine dioxide.

In using the methods of this invention, a gel composition comprising a gel containing 1 to 5,000 ppm of chlorine dioxide can be prepared.

The herein disclosed invention contemplates a chlorine dioxide and gel product prepared by the process of preparing a solution of chlorine dioxide and adding said solution of chlorine dioxide to gum thickener or adding the gum thickener to the chlorine dioxide solution to form a concentrated chlorine dioxide gel composition.

The gels of this invention can form a disinfectant composition comprising a gel containing an effective amount of chlorine dioxide which can be used in a method of disinfecting comprising applying to the area to be disinfected a composition of a gel and chlorine dioxide wherein the chlorine dioxide is in the range of 1 to 5,000 ppm.

EXAMPLES OF PREPARATION

Gels containing various concentrations of chlorine dioxide have been prepared directly by thickening aqueous solutions of chlorine dioxide with guar gum, xanthan gum, mixtures of the two, as well as sodium carboxymethylcellulose.

Guar gum was added to 3000 ppm chlorine dioxide at levels ranging from 0.5 to 3.0 g to 100 cc chlorine dioxide solution to produce a mix ranging from a thick liquid to a viscous gel. The gel has an extremely pleasant, silky hand, and would be very acceptable for topical use as a bactericide, fungicide or viricide. The gel is stable in an enclosed system but slowing loses chlorine dioxide by volitization on exposure to the atmosphere.

Stable gels can be prepared from chlorine dioxide solutions ranging from 1 to 6000 ppm and xanthan gum levels ranging from 0.1 to 5.0 g/100 cc solution. The composition of the gels range from a thick, flowable liquid, to a gel dry to the touch. Increasing gum content tends to help maintain the stability of the chlorine dioxide concentration in the gel through the acidity inherent in the xanthan gum, as well as the increased viscosity reducing the rate of diffusion and, therefore, the volatility of the chlorine dioxide contained in the gel to reduce loss to the atmosphere.

Gels prepared from aqueous chlorine dioxide solutions with concentrations up to 4500 ppm retained over 74% of the original chlorine dioxide concentration over a 6 month period. Most loss was to the headspace of the container.

Various amounts of xanthan gum were added to a 2825 ppm solution of aqueous chlorine dioxide. Systems with higher xanthan gum content appear to be more stable than the systems with lower xanthan content. Xanthan gum is a biologically generated polysaccharide which has a repeating organic acid group as part of its structure. The increased stability of high xanthan content systems suggest that the xanthan is contributing to the increased stability, and it can be assumed that the acid functionality was the cause.

Xanthan gum was mixed with dilute sodium chlorite, and within 2–4 hours, the system had generated 50–75 ppm chlorine dioxide. It was observed that concentrated chlorite solution actually generates less chlorine dioxide than does dilute chlorite solution. It was most probably due to the alkalinity in the chlorite which reacts with and neutralizes the acid functionality of the xanthan gum, which acid functionality is responsible for conversion of chlorite to chlorine dioxide.

Stable chlorine dioxide gels are prepared by adding the appropriate thickeners to aqueous solutions of chlorine dioxide with agitation. Agitation can range from vigorous hand shaking, to the use of mechanical blenders. The chlorine dioxide solution can be prepared by any of the methods commonly used to generate this oxidant, including acid/chlorite generators, chlorine/chlorite, generators, or acid/hypochlorite/chlorite generators. The chlorine dioxide may also be prepared by a dry mix method (claimed in a companion application: Attorney Docket No. 99017-PA). In the dry mix method, a solution and reaction of the dry components in the appropriate volume of water is prepared before addition of the thickener. The gel may also be prepared by dissolving a dry mix consisting of the components of the above cited dry mix to which has been added the appropriate quantity of dry powdered thickener. This dry mix can be stored until such time as the gel is prepared. The chlorine dioxide is prepared and the gelling action started in one step by addition of the appropriate volume of water to the mix. Chlorine dioxide is generated rapidly by this dry mix before the gel reaches the point where the solid components are fixed in the gel and unable to dissolve and interact. It is to be noted that stable gels with several thousand ppm of chlorine dioxide content can also be prepared from chlorine dioxide solutions and sodium carboxymethylcellulose and guar gum.

Chlorine dioxide gel preparation can be performed with aqueous solutions of chlorine dioxide generated from solid 80% sodium chlorite converted to chlorine dioxide by the process (dry mix).

In an experiment guar gum was added to 404 ppm chlorine dioxide and mixed to form a yellow, viscous gel. The gel was stable for over 72 hours. A similar mix without the chlorine dioxide was viscous on mixing, but liquefied within 2 hours. This experiment shows chlorine dioxide stabilizes guar gum gel, and that guar gum does not react significantly with chorine dioxide.

In another preparation, guar gum levels from 0.04 to 0.4 g guar gum in 25 cc of 404 ppm chlorine dioxide gave an increase in viscosity from a soupy liquid to a thick gel without any decrease in chlorine dioxide concentration; again showing a lack of reaction between guar gum and chlorine dioxide, as well as versatility in selection of the viscosity of the final gel.

Gels formed from aqueous chlorine dioxide and xanthan gum can be formed from solutions containing chlorine dioxide of up to and beyond 4500 ppm, with xanthan gum additions ranging from 0.1 to over 5 g/100 cc solution. These mixtures can result in a thickened free flowing liquid; up to a gel which is dry to the touch.

The gels prepared by this invention have many applications. For example, the xanthan gum used is food grade, and thus nontoxic. Accordingly, the chlorine dioxide gels can be applied to the skin to combat topical infections such as athletes foot, corns, warts or simple abrasions. The gels have a pleasant hand, and leave a thin film of dried xanthan gel. The chlorine-like odor of the chlorine dioxide can be masked with a fragrance to make it more appealing for individual use.

The gels can also be used to sterilize or deodorize atmospheres. In test-use a small, one inch in diameter sized sample of thickened 2425 ppm chlorine dioxide gel was placed in a small bottle cap, and dropped into a 1 liter wide mouthed bottle containing a wet starch iodine test strip fastened to the side of the top of the bottle. The test strip turned blue immediately, demonstrating significant expulsion of chlorine dioxide vapor from the gel.

A similar quantity of 2425 ppm gel was placed on the top shelf of a refrigerator, with a wet starch iodide test strip on the bottom shelf The refrigerator door was closed, then opened in 15 minutes, at which time the test strip was blue, indicating chlorine dioxide vapors had already dispersed throughout the volume of the refrigerator.

Another sample of this 2425 ppm gel was spread in a shallow 2" wide bottle cap and placed on the desktop exposed to ambient atmosphere. The gel lost all color and odor within 5 hours. A similar mix was placed in a small 200 ml wide mouth bottle and allowed to sit overnight in a hood exposed to the rapidly moving atmosphere. The next day, the top layer of the gel had lost its yellow color and characteristic chlorine dioxide odor. The bottle was capped and allowed to sit for 16 hours, after which time, the yellow color had returned to the top, and chlorine dioxide odor could again be detected. The bottle was then allowed to sit open in the hood overnight. As before, the yellow color disappeared from the top of the gel. This depleted system was then placed on the top shelf of the refrigerator, with wet starch iodide test paper on the bottom. The paper turned blue in 30 minutes, demonstrating continued loss of sufficient chlorine dioxide vapor through the depleted top of the gel to deodorize or disinfect the space.

Preparation of more concentrated chlorine dioxide systems can be accomplished by the generation of chlorine dioxide by one of the commonly used methods prior to the addition of the gelling agent. In addition to the well known routes for generation of chorine dioxide, the chorine dioxide used to prepare the gel can be prepared by a dry mix method. Aqueous chlorine dioxide prepared by the dry mix process was mixed with xanthan gum. As the gum level increased from 1.0 to 2.18 g/100 cc of 3035 ppm chlorine dioxide, the stability of the gel improved, and some of the systems actually generated a small increase in chlorine dioxide over a 3 day period. It appears that these systems are expected to be very shelf-stable, and no activator or stabilizer beyond the natural organic acid functionality of the xanthan gum is needed to maintain stability of these gels. It appears that most of any observed losses take place by volatilization of the chlorine dioxide into head space in the containers used to store the gel. Sealed in an opaque tube like a toothpaste, losses would be expected to be much lower.

Comparing these gels to the chlorine dioxide solution used to prepare them, the gels retained higher chlorine dioxide levels with time, indicating no degrading reactions, as well as the high viscosity of the gels apparently reducing the volatility and diffusion of the gaseous chlorine dioxide so that transfer from the aqueous gelled phase to the atmosphere does not take place as rapidly as from the nongelled aqueous phase to any head space in their containers. This property can be useful in applications where the gel is used as a continuing source of low levels of chlorine dioxide vapor.

The inventor has carried out experiments on systems in which the chlorine dioxide is already generated, and a concentrated solution is subsequently thickened with xanthan gum. Aliquots of concentrated chlorine dioxide solution were thickened with various quantities of xanthan gum, and the chlorine dioxide content of the gels determined at the time of mixing. The gels were stored in clear glass wide mouth bottles in the dark, periodically removed and the chlorine dioxide levels determined over a period of 78 days. A solution containing 1 g xanthan gum/100 cc solution measured 4250 ppm at the time of mixing, and 3210 ppm 78 days later. A gel containing 1.6 g xanthan gum/100 cc solution measured 3575 ppm at the time of mixing, and contained 2927 ppm 78 days later. A third gel containing 2.2 g xanthan gum/100 cc measured 4115 ppm at the time of mixing, and 2604 ppm 78 days later. All of these gels were contained in wide mouth bottles with some head space above the gel, so that chlorine dioxide was free to vaporize into the head space. Each time the bottles were opened, some chlorine dioxide was lost. The inventor believes this is responsible for the major part of the drop in concentration, and if the gel were in a tube like tooth paste, where there was no head space, the loss would be insignificant over a 8 month period.

The chlorine dioxide gels are stable to wide variations of temperature. A gel was frozen in dry ice, and then warmed to 158 F, with no loss in gel properties.

Using commercially available xanthan gum, the inventor was able to make mixtures ranging from a thick yellow liquid, to a thick gel which was almost dry to the touch. All gel compositions have retained the bright yellow color characteristic of chlorine dioxide for over eight (8) months in clear glass bottles exposed to laboratory light, and there is no reason to believe that the gels are experiencing any significant loss of chlorine dioxide.

The herein disclosed chlorine dioxide gels have great potential for treatment of topical conditions caused by bacteria, fungus and viruses.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A method for preparing a chlorine dioxide gel consisting of the steps of preparing a solution of chlorine dioxide and adding said solution of chlorine dioxide to a gum thickener to form a gel containing chlorine dioxide.

2. A gel composition consisting of a gel containing 1 to 5,000 ppm of chlorine dioxide prepared by the method of claim 1.

3. A disinfectant or deodorant composition consisting of a gel containing an effective amount of chlorine dioxide prepared by the method of claim 1.

4. A method of disinfecting consisting of applying to the area to be disinfected a composition of a gel and chlorine dioxide wherein the chlorine dioxide is in the range of 1 to 5,000 ppm and has been prepared by the method of claim 1.

5. The method of disinfecting of claim 4 wherein the area to be disinfected is the skin.

6. A method for preparing a chlorine dioxide gel consisting of the steps of preparing a solution of chlorine dioxide and adding a gum thickener to said solution of chlorine dioxide to form a gel containing chlorine dioxide.

7. A chlorine dioxide and gel product prepared by the process consisting of preparing a solution of chlorine dioxide and adding said solution of chlorine dioxide to gum thickener or adding the gum thickener to the chlorine dioxide solution to form a concentrated chlorine dioxide gel composition.

8. A gel composition consisting of an effective amount of chlorine dioxide in a gel.

9. A gel composition consisting of a gel containing at least 2425 ppm of chlorine dioxide.

10. A chlorine dioxide gel composition comprising a gel and chlorine dioxide in the approximate range of 0.04 to 0.4 g of gum in 25 cc of 404 ppm of chlorine dioxide.

* * * * *